US006440946B1

(12) United States Patent
Kiso et al.

(10) Patent No.: US 6,440,946 B1
(45) Date of Patent: Aug. 27, 2002

(54) MULTIPLE-AGENTS-BINDING COMPOUND, PRODUCTION AND USE THEREOF

(75) Inventors: Yoshiaki Kiso, Osaka; Masahiko Fujino, Hyogo, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/370,543

(22) Filed: Aug. 9, 1999

(30) Foreign Application Priority Data

Feb. 25, 1999  (JP) ........................................... 11-047557

(51) Int. Cl.⁷ ............................................... A61K 31/70
(52) U.S. Cl. ............................ 514/45; 514/46; 514/47; 514/48; 514/49; 514/50; 514/51; 514/220; 514/230.5; 514/252; 514/253
(58) Field of Search .............................. 514/45, 46, 47, 514/48, 49, 50, 51, 885, 220, 230.5, 252, 253

(56) References Cited

U.S. PATENT DOCUMENTS

| | | | |
|---|---|---|---|
| 5,132,414 A | * | 7/1992 | Rosowsky et al. |
| 5,650,412 A | * | 7/1997 | Kim et al. |
| 5,760,013 A | * | 6/1998 | Hwu et al. |
| 5,807,841 A | * | 9/1998 | Huff et al. |
| 5,977,086 A | * | 11/1999 | Lisziewicz et al. |

FOREIGN PATENT DOCUMENTS

WO    WO98/43995 A    10/1998

OTHER PUBLICATIONS

In Japanese only, Y. Kiso et al., "New Anti–HIV Agent, Conjugate of HIV..." *12th Annual Meeting of AIDS Society of Japan*, Dec. 1 & 2, 1998.
In Japanese only, T. Matsuda et al., "A New Class of Potent Anti–HIV Agents,..." *18th Symposium on Medicinal Chemistry 7th Annual Meeting of Division of Medicinal Chemistry*, Nov. 25–27, 1998.
In Japanese only, T. Matsuda et al., "Synthesis and Activity of a New Type of Anti–HIV Agents, . . ." *35th Peptide Forum*, Oct. 7–9, 1998.

* cited by examiner

*Primary Examiner*—James O. Wilson
(74) *Attorney, Agent, or Firm*—Mark Chao; Elaine M. Ramesh

(57) ABSTRACT

The present invention is to provide a multiple-agents-binding compound comprising a compound having anti-HIV activity and having no affinity for cell surface protein bound together with a same or different kind of at least one compound having anti-HIV activity and having no affinity for cell surface protein, or a salt thereof, and a pharmaceutical composition for the prevention or treatment of infectious diseases of HIV or AIDS comprising said multiple-agents-binding compound.

24 Claims, No Drawings

MULTIPLE-AGENTS-BINDING COMPOUND, PRODUCTION AND USE THEREOF

FIELD OF THE INVENTION

The present invention relates to a multiple-agents-binding compound comprising a compound having anti-HIV activity bound together with at least one compound having anti-HIV activity and a pharmaceutical composition comprising said multiple-agents-binding compound.

BACKGROUND OF THE INVENTION

It is known that HIV (human immunodeficiency virus) causes various clinical symptoms such as AIDS (acquired immunological deficient syndrome), AIDS-related syndromes, etc. In order to treat the above-mentioned symptoms, HIV protease inhibitors have recently been developed in addition to HIV reverse transcriptase inhibitors which have been used so far. However, most of these anti-HIV agents and in particular peptide compounds of HIV protease inhibitors have a lot of problems such as water insolubility, instability in vivo, low oral absorption, etc. Moreover, since a large amount of these anti-HIV agents are administered for a long time, development of an anti-HIV agent showing superior bioavailability when oral administration is desired. Furthermore, since known anti-HIV agents have problems such as side effects, the advent of drug-resistant virus, etc., an antagonist of CCR5 which is the second receptor from which macrophage-tropic HIV invades to a target cell and an antagonist of CXCR4 which is the second receptor from which T cell-tropic HIV invades to a target cell are being developed, as new anti-HIV agents having different mechanisms. On the other hand, combination use of HIV reverse transcriptase inhibitors with HIV protease inhibitors provides further progress of the treatment of AIDS. However, said combination use is not sufficient for the eradication of AIDS.

OBJECT OF THE INVENTION

Cocktail therapy such as combination of HIV reverse transcriptase inhibitor and HIV protease inhibitor is known to be effective for the treatment of AIDS. However, side effects caused by administration of these agents in large amounts and for a long time are not reduced. In addition thereto, according to said therapy, there are many problems in administration of these agents such as complexity of administration time or dose, etc. The present invention is to provide an anti-HIV agent which has more potent anti-HIV activity, which is improved in absorption when orally administered, stability, physicochemical properties, etc., ease of treatment and which reduces toxicity according to reduction of dose.

SUMMARY OF THE INVENTION

The present inventors diligently made extensive studies on solving the above-mentioned problems and, as a result, they found that a complex obtained by binding the same or different kind of two or more compounds to each other, said compounds being selected from compounds having anti-HIV activity and having no affinity for cell surface protein such as HIV reverse transcriptase inhibitor, HIV protease inhibitor, CCR5 antagonist, etc., shows superior anti-HIV activity and at the same time it has clinically desirable pharmaceutical effects such as improvement of absorption when orally administered, reduction of side effects according to reduction of dose, etc. Moreover, the compounds of the present invention can be substituted for conventional cocktail therapy and can be used more simply and effectively. Based on these findings, the present invention was accomplished.

More specifically, the present invention relates to
(1) a compound (or complex) comprising a compound having anti-HIV activity and having no affinity for cell surface protein bound together with (or conjugated with) a same or different kind of at least one compound having anti-HIV activity and having no affinity for cell surface protein, or a salt thereof;
(2) a compound obtained by binding two compounds to each other, said compounds being selected from HIV reverse transcriptase inhibitor, HIV protease inhibitor or CCR5 antagonist, or a salt thereof;
(3) a compound of the above (1), wherein the compound having anti-HIV activity is HIV reverse transcriptase inhibitor, HIV protease inhibitor or CCR5 antagonist;
(4) a compound of the above (1), wherein at least one of the compounds having anti-HIV activity is CCR5 antagonist;
(5) a compound of the above (2), wherein the two compounds are HIV reverse transcriptase inhibitor and HIV protease inhibitor;
(6) a compound of the above (2), (3) or (5), wherein the HIV reverse transcriptase inhibitor is nucleoside reverse transcriptase inhibitor having at least one hydroxy group or a derivative thereof;
(7) a compound of the above (2), (3) or (5), wherein the HIV reverse transcriptase inhibitor is zidovudine, didanosine, zalcitabine, lamivudine, stavudine or abacavir;
(8) a compound of the above (2), (3) or (5), wherein the HIV reverse transcriptase inhibitor is zidovudine;
(9) a compound of the above (2), (3) or (5), wherein the HIV protease inhibitor is a compound having at least one hydroxy group, amino group and/or carboxyl group and mimicking transition-state of a substrate of HIV protease;
(10) a compound of the above (2), (3) or (5), wherein the HIV protease inhibitor is saquinavir, ritonavir, indinavir, nelfinavir, a compound of the formula:

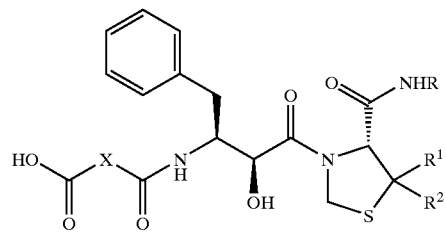

wherein R is a $C_{1-6}$ alkyl group or an optionally substituted phenyl-$C_{1-3}$ alkyl group, $R^1$ and $R^2$ are independently a hydrogen atom or a $C_{1-6}$ alkyl group, and X is an optionally substituted $C_{1-6}$ alkylene group, a compound of the formula:

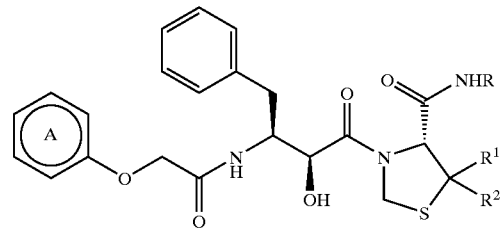

wherein R is a $C_{1-6}$ alkyl group or an optionally substituted phenyl-$C_{1-3}$ alkyl group, $R^1$ and $R^2$ independently a hydrogen atom or a $C_{1-6}$ alkyl group, and the ring A is an optionally substituted benzene ring, or a salt thereof;

(11) a compound of the above (2), (3) or (5), wherein the HIV protease inhibitor is a compound of the formula:

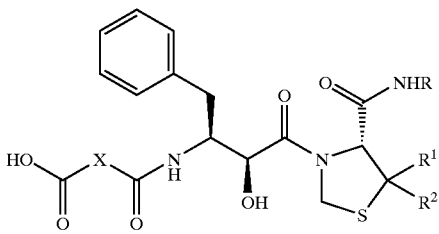

wherein each symbol is as defined in the above (10), a compound of the formula:

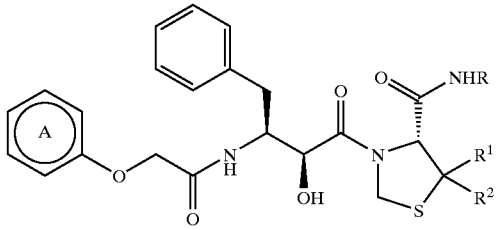

wherein each symbol is as the above (10), or a salt thereof;

(12) a compound of the above (1) or (2), wherein the compound having anti-HIV activity and having no affinity for cell surface protein such as HIV reverse transcriptase inhibitor, HIV protease inhibitor, CCR5 antagonist, etc. binds to a same or different kind of at least one compound having anti-HIV activity and having no affinity for cell surface protein, directly or through a spacer;

(13) a compound of the above (12), wherein the spacer has at least two carboxyl groups;

(14) a compound of the above (5), which is a compound of the formula:

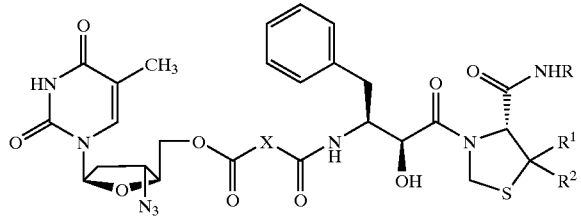

wherein each symbol is as defined in the above (10), a compound of the formula:

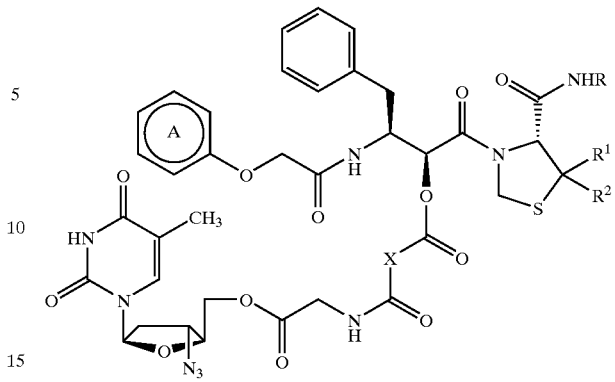

wherein each symbol is as defined in the above (10), or a salt thereof;

(15) a compound of the above (10), (11) or (14), wherein R is (1) a benzyl group substituted with a $C_{1-3}$ alkyl group or (2) a t-butyl group, $R^1$ and $R^2$ are independently a hydrogen atom or a methyl group, and X is a group of the formula: $—(CH_2)_m—$ (m is an integer of 1–3) in which a methylene at an optional position may be substituted with a methyl group;

(16) a pharmaceutical composition which comprises a compound of the above (1) or (2), or a salt thereof;

(17) a composition of the above (16) which is for oral administration;

(18) a composition of the above (16) which is for the prevention or treatment of infectious disease of HIV;

(19) a composition of the above (16) which is for the prevention or treatment of AIDS; etc.

DETAILED DESCRIPTION OF THE INVENTION

The above-mentioned "anti-HIV activity" means that HIV infection is inhibited, HIV proliferation is inhibited, the number of HIV is reduced, etc.

Examples of the "compound having anti-HIV activity and having no affinity for cell surface protein" include a compound having anti-HIV activity and having no affinity for HIV surface protein gp120 and/or HIV target cell surface protein CD4, for example, HIV reverse transcriptase inhibitor; HIV protease inhibitor; chemokine antagonist such as CCR5 antagonist, CXCR4 antagonist, etc.; APJ receptor ligand (for example, apelin, etc.), AIDS vaccine (for example, HIV-1-gp-120 vaccine, etc.), antimetabolite (metabolic antagonist) (for example, ribavirin, hydroxycarbamide, peldesine, etc.), DNA polymerase inhibitor (for example, lobucavir, phosfazid, etc.), immunostimulant (for example, interleukin-2, interleukin-12, colony stimulating factor, interferon α, glycyrrhizin, tucaresol, maitake-glucan, procaine, etc.), etc. Among others, HIV reverse transcriptase inhibitor, HIV protease inhibitor, chemokine antagonist such as CCR5 antagonist, CXCR4 antagonist, etc., APJ receptor antagonist, etc. are preferable, and in particular, HIV reverse transcriptase inhibitor, HIV protease inhibitor, CCR5 antagonist, etc. are preferable.

The "multiple-agents-binding compound" of the present invention is a compound (or complex) comprising a compound having anti-HIV activity and having no affinity for cell surface protein bound together with (or conjugated with) a same or different kind of at least one compound having anti-HIV activity and having no affinity for cell surface protein, wherein each of the compound having anti-HIV activity and having no affinity for cell surface protein is selected from the above-mentioned compounds; and each compound, which constitutes the "multiple-agents-binding compound" and which is cleaved and released from the "multiple-agents-binding compound" in vivo, shows superior anti-HIV activity.

The "double-agents-binding compound" of the present invention is a compound (or complex) wherein the compound having anti-HIV activity and having no affinity for cell surface protein selected from the class consisting of HIV reverse transcriptase inhibitor, HIV protease inhibitor and CCR5 antagonist chemically binds to a same or different kind of the compound having anti-HIV activity and having no affinity for cell surface protein, directly or through a spacer; and each compound, which constitutes the "double-agents-binding compound" and which is cleaved and released from the "multiple-agents-binding compound" in vivo, shows superior anti-HIV activity.

More preferably, the "double-agents-binding compound" is constituted by the compound having anti-HIV activity and having no affinity for cell surface protein selected from the class consisting of HIV reverse transcriptase inhibitor and HIV protease inhibitor, and further preferably, the "double-agents-binding compound" is constituted by one compound selected from HIV reverse transcriptase inhibitor and another compound selected from HIV protease inhibitor.

As the HIV reverse transcriptase inhibitor, any substance can be employed as far as it inhibits activity of reverse transcriptase of HIV, and either nucleoside or non-nucleoside derivatives can be employed.

Examples of the inhibitor which is a nucleoside derivative include a compound consisting of a pyrimidine base, a purine base, an imidazole base or a triazole base and furanose or its acyclo derivative having at least one hydroxy group, or a derivative thereof.

Examples of the inhibitor include zidovudine (3'-azido-3'-deoxythymidine: AZT), didanosine (2',3'-dideoxyinisine: ddI), zalcitabine (2',3'-dideoxycytidine: ddC), lamivudine (3'-thia-2',3'-dideoxycytidine: 3TC), stavudine (2',3'-didehydro-2',3'-dideoxythymidine: d4T), 3'-thia-2',3'-dideoxy-5-fluorocytidine (FTC), lodenosine (2'-β-fluoro-2',3'-dideoxyadenosine), abacavir, etc. The above-mentioned inhibitor is a non-natural nucleoside or a nucleoside derivative, which is taken into DNA when HIV synthesizes DNA by reverse transcription of RNA and, as a result, inhibits DNA synthesis. Examples of the nucleoside derivative include a compound which has a structure similar to a nucleoside and wherein a part of atoms constituting the nucleoside is lacking or is substituted with other atoms (for example, a furanose moiety of a nucleoside is converted to a cyclopentane ring, the other heterocyclic ring group, etc.), etc.

Examples of the inhibitor which is a non-nucleoside derivative include delavirdine, loviride, calanolide A, etc.

As the HIV reverse transcriptase inhibitor, HIV reverse transcriptase inhibitor which is a nucleoside derivative is preferable. Among others, zidovudine, didanosine, zalcitabine, lamivudine, stavudine, abacavir, etc. are preferable, and in particular, zidovudine is preferable.

Examples of the HIV protease inhibitors include a substance inhibiting protease activity of HIV such as a compound mimicking transition-state of a substrate of HIV protease, etc.

Examples of the compound mimicking transition-state of a substrate include a substance, which is capable of binding to a binding site of an enzyme (protease) to a substrate and which has a structure similar to the substrate in the enzyme-substrate complex, such as saquinavir, ritonavir, indinavir, nelfinavir, amprenavir, palinavir, lasinavir, CGP57813 (35th ICAAC Abstracts I217 (1995)), BMS232632 (38th ICAAC Abstracts I242 (1998)), DMP-450, tiplanavir (J. Med. Chem., 41, 3468 (1998) ), lopinavir (WHO Drug Infomation, 12 (4), 266 (1998)), a compound of the formula (I):

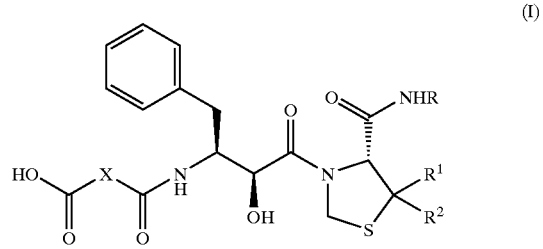

(wherein each symbol is as defined above) or a salt thereof (for example, KNI-272, KNI-357, KNI-391, KNI-413, KNI-417, KNI-418, KNI-547, KNI-549, KNI-689, KNI-690, KNI-691, KNI-852, etc. (Chem. Pharm. Bull. ,40,2251 (1992); Arch. Pharm. Pharm. Med. Chem. ,331, 87 (1998); Japanese Patent Unexamined Publication No. 1996-259532, Japanese Patent Unexamined Publication No. 1998-25242, Japanese Patent Unexamined Publication No. 1998-101654)), a compound of the formula (III):

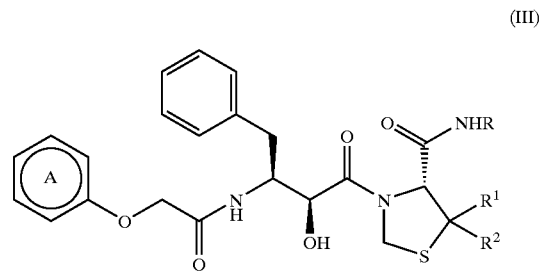

(wherein each symbol is as defined above) or a salt thereof (for example, compounds described in J. Med. Chem., 42, 1789 (1999)), etc.

As the HIV protease inhibitor, compounds having at least one hydroxy group, amino group and/or carboxyl group and mimicking transition-state of a substrate of HIV protease is preferable. Among others, saquinavir, ritonavir, indinavir, nelfinavir, a compound of the formula (I) or (III) or a salt thereof, etc. are preferable, and a compound of the formula (I) or (III) or a salt thereof is more preferable (in particular, KNI-413, KNI-689, KNI-690, KNI-691, KNI-727, KNI-852, etc. are preferable) but the HIV protease inhibitor to be used in the present invention is not limited thereto.

As the HIV reverse transcriptase inhibitor and HIV protease inhibitor, those available on the market or those prepared by known synthetic methods can be employed.

Examples of the CCR5 antagonist include a compound which inhibits or regulates invasion of macrophage-tropic HIV to a target cell through CC chemokine type 5 receptor (CCR5), for example, a compound antagonizes binding of RANTES as a natural ligand to CCR5. More specifically, compounds described in PCT/JP98/05708 (WO99/32100) [preferably, N,N-Dimethyl-N-(4-(((2-(4-methylphenyl)-6,7-dihydro-5H-benzocyclohepten-8-yl)carbonyl)amino) benzyl)-N-(4-tetrahydropyranyl)ammonium chloride, etc.];

compounds described in Japanese Patent Application Nos. 1998-234388, 1999-127724, 1999-170212, 1999-170345, etc.; compounds described in NSC-651016 (J. Med. Chem., 41, 2184 (1998)), WO98/25604, WO98/25605, WO98/25617, WO98/27815, WO98/30218, WO98/31364, WO99/1127, WO99/4797, WO99/9984, WO99/14378, etc. but the CCR5 antagonists are not limited to those described in these references.

In the compound of the present invention, a compound having anti-HIV activity is bound together with a same or different kind of at least one compound having anti-HIV activity, wherein each of the compound having anti-HIV activity is selected from the above-mentioned compounds, and said compounds constituting the compound of the present invention chemically binds to each other, directly or through a spacer. Such chemical binding may be any one as far as it is cleaved in vivo to be capable of releasing each compound having anti-HIV activity and constituting the compound of the present invention. Examples of the chemical binding include ester linkage, amide linkage, ether linkage, disulfide linkage, etc.

As the chemical binding, ester linkage, which is capable of being cleaved by esterase, etc. existing in blood or target cells in vivo to which the compound of the present invention is carried and which is capable of releasing the above-mentioned compound having anti-HIV activity near its action point, is preferable. Among others, a linkage, which is not easily cleaved while the compound of the present invention is carried to the action points and which has stability to such a degree that the linkage is gradually cleaved in blood or in target cells, is more preferable but a linkage to be employed in the present invention is not limited thereto.

Binding site where the compounds having anti-HIV activity constituting the multiple-agents-binding compound or the double-agents-binding compound bind to each other varies depending on kind of said compound having anti-HIV activity. When said compound having anti-HIV activity has carboxyl group, hydroxy group and/or amino group, a chemical binding such as ester linkage, amide linkage, etc. formed through these functional groups are preferably employed. In particular, ester linkage where carboxyl group and hydroxy group are chemically bound is preferably employed. In addition, said functional group may play an important role for the expression of the activity in the compound having anti-HIV activity and said functional group may be present at any position of the compound having anti-HIV activity, since said chemical binding is cleaved in vivo to convert into a free form.

In the above formula (I) or (III), examples of the "$C_{1-6}$ alkyl group" represented by R include a straight or branched alkyl group, for example, methyl, ethyl, propyl, isopropyl, butyl, isobutyl, sec-butyl, t-butyl, pentyl, isopentyl, neopentyl, hexyl, etc. and preferably t-butyl.

Examples of the "phenyl-$C_{1-3}$ alkyl group" in the "optionally substituted phenyl-$C_{1-3}$ alkyl group" represented by R include, for example, benzyl, phenethyl, phenylpropyl, etc. and preferably benzyl.

Examples of "substituents", which the "phenyl-$C_{1-3}$ alkyl group" in the "optionally substituted phenyl-$C_{1-3}$ alkyl group" represented by R may have and which the "benzene ring" in the "optionally substituted benzene ring" represented by A may have, include, for example, halogen, nitro, cyano, a $C_{1-6}$ alkyl group, an optionally substituted hydroxy group, an optionally substituted thiol group, an optionally substituted amino group, etc., and the number of the substituents is preferably 1–3.

Examples of the halogen as the substituent for R and A include fluorine, chlorine, bromine, iodine, etc.

Examples of the $C_{1-6}$ alkyl group as the substituent for R and A include a straight or branched alkyl group, for example, methyl, ethyl, propyl, isopropyl, butyl, isobutyl, sec-butyl, t-butyl, pentyl, isopentyl, neopentyl, hexyl, etc. and preferably methyl.

Examples of the substituent in the optionally substituted hydroxy group as the substituent for R and A include a $C_{1-6}$ alkyl group (for example, methyl, ethyl, propyl, isopropyl, butyl, isobutyl, sec-butyl, t-butyl, pentyl, isopentyl, neopentyl, hexyl, etc.), etc.

Examples of the substituent in the optionally substituted thiol group as the substituent for R and A include the substituent as the above "substituent in the optionally substituted hydroxy group as the substituent for R and A".

Examples of the substituent in the optionally substituted amino group as the substituent for R and A include, in addition to the same substituent as the above "substituent in the optionally substituted hydroxy group as the substituent for R and A", an acyl group (for example, $C_{2-4}$ alkanoyl (e.g., acetyl, propionyl, butyryl, etc.), $C_{1-4}$ alkylsulfonyl (e.g., methanesulfonyl, ethanesulfonyl, etc.), etc.), etc.

Examples of the "$C_{1-6}$ alkyl group" represented by $R^1$ and $R^2$ include straight or branched one such as methyl, ethyl, propyl, isopropyl, butyl, isobutyl, sec-butyl, t-butyl, pentyl, isopentyl, neopentyl, hexyl, etc., and preferably methyl.

Examples of the "$C_{1-6}$ alkylene group" in the "optionally substituted $C_{1-6}$ alkylene group" represented by X include, for example, methylene, ethylene, propylene, etc., and preferably ethylene, propylene, etc.

Examples of the substituent for the "$C_{1-6}$ alkylene group" in the "optionally substituted $C_{1-6}$ alkylene group" represented by X include, for example, nitro, cyano, a $C_{1-6}$ alkyl group, an optionally substituted hydroxy group, an optionally substituted thiol group, an optionally substituted amino group, etc., and the number of the substituents is preferably 1–3.

Examples of the "$C_{1-6}$ alkyl group" as the substituent for X include straight or branched chains such as methyl, ethyl, propyl, isopropyl, butyl, isobutyl, sec-butyl, t-butyl, pentyl, isopentyl, neopentyl, hexyl, etc., and preferably methyl.

Examples of the substituent in the "optionally substituted hydroxy group" as the substituent for X include $C_{1-6}$ alkyl group (for example, methyl, ethyl, propyl, isopropyl, butyl, isobutyl, sec-butyl, t-butyl, pentyl, isopentyl, neopentyl, hexyl, etc.), etc.

Examples of the substituent in the optionally substituted thiol group as the substituent for X include the same substituent as the above "substituent in the optionally substituted hydroxy group as the substituent for X".

Examples of the substituent in the optionally substituted amino group as the substituent for X include, in addition to the same substituent as the above "substituent in the optionally substituted hydroxy group as the substituent for X", an acyl group (for example, $C_{2-4}$ alkanoyl (e.g., acetyl, propionyl, butyryl, etc.), $C_{2-4}$ alkylsulfonyl (e.g., methanesulfonyl, ethanesulfonyl, etc.), etc.), etc.

Preferred examples of X include —$(CH_2)_m$— (m is an integer of 1–3) in which any methylene at an optional position may be substituted with a methyl group, and specific examples include —$CH_2$—, —$CH_2$—$CH_2$—, —$CH(CH_3)$—$CH_2$—, —$C(CH_3)_2$—$CH_2$—, —$CH(CH_3)$—$CH(CH_3)$—, —$CH_2$—$CH_2$—$CH_2$—, etc.

As the compound of the present invention, the double-agents-binding compound comprising the compound having anti-HIV activity and having no affinity for cell surface protein selected from the class consisting of HIV reverse transcriptase inhibitor, HIV protease inhibitor and CCR5 antagonist binds to a same or different kind of at least one compound having anti-HIV activity and having no affinity for cell surface protein selected from the class consisting of HIV reverse transcriptase inhibitor, HIV protease inhibitor and CCR5 antagonist, directly or through a spacer, or a salt thereof is preferable.

Among others, a compound of the formula (II):

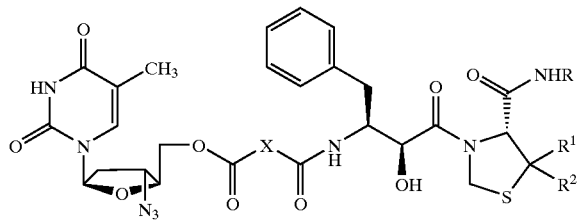

wherein R is a $C_{1-6}$ alkyl group (preferably, t-butyl group) or an optionally substituted phenyl-$C_{1-3}$ alkyl group (preferably, a benzyl group substituted with a $C_{1-3}$ alkyl group), $R^1$ and $R^2$ are independently a hydrogen atom or a $C_{1-6}$ alkyl group (preferably, methyl group), and X is an optionally substituted $C_{1-6}$ alkylene group (preferably, —$(CH_2)_m$— (m is an integer of 1–3) in which any methylene at an optional position may be substituted with a methyl group, or a salt thereof; or a compound of the formula (IV):

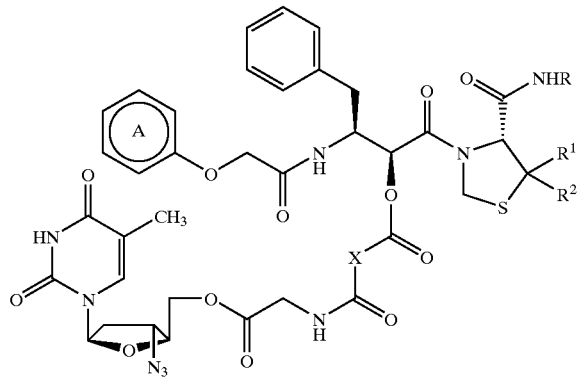

wherein R is a $C_{1-6}$ alkyl group (preferably, t-butyl group) or an optionally substituted phenyl-$C_{1-3}$ alkyl group (preferably, a benzyl group substituted with a $C_{1-3}$ alkyl group), $R^1$ and $R^2$ are independently a hydrogen atom or a $C_{1-6}$ alkyl group (preferably, methyl group), X is an optionally substituted $C_{1-6}$ alkylene group (preferably, —$(CH_2)_m$— (m is an integer of 1–3) in which any methylene at an optional position may be substituted with a methyl group, and the ring A is an optionally substituted benzene ring (preferably, a benzene ring substituted with 1–2 $C_{1-3}$ alkyl groups), or a salt thereof is preferable.

Examples of the salts of the compound of the present invention include a pharmaceutically acceptable salt such as a salt with inorganic base, a salt with organic base, a salt with inorganic acid, a salt with organic acid, a salt with basic or acidic amino acid, etc. Examples of the salt with the inorganic base include a salt with alkali metal (e.g. sodium, potassium, etc.), alkaline earth metal (e.g. calcium, magnesium, etc.), aluminum, ammonia, etc. Examples of the salt with the organic base include a salt with trimethylamine, triethylamine, pyridine, picoline, ethanolamine, diethanolamine, triethanolamine, dicyclohexylamine, N,N'- dibenzylethylenediamine, etc. Examples of the salt with the inorganic acid include a salt with hydrochloric acid, hydrobromic acid, nitric acid, sulfuric acid, phosphoric acid, etc. Examples of the salt with the organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Examples of the salt with the basic amino acid include a salt with arginine, lysine, ornithine, etc. Examples of the salt with the acidic amino acid include a salt with aspartic acid, glutamic acid, etc.

The compound of the present invention may be hydrated or solvated. When the compound of the present invention exists as configuration isomer, diastereomer, conformer, etc., it is possible to isolate individual isomers with per se known separation and purification method, if desired. When the compound of the present invention is racemate, it can be separated into (S)-compound and (R)-compound with usual optical resolution and individual optical isomers and a mixture thereof are included in the scope of the present invention.

The compound of the present invention or a salt thereof alone or as an admixture with a pharmaceutically acceptable carrier (e.g. solid formulations such as tablets, capsules, granules, powders, suppositories, etc.; liquid formulations such as syrups, injections, etc.) may be orally or non-orally administered.

Examples of the carriers include various organic or inorganic carriers which are generally used in this field. For example, an excipient, a lubricant, a binder, an disintegrating agent, a base for suppository, etc. are used in the solid formulations, and a solvent, a solubilizer, a suspending agent, a isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of the excipient include lactose, sucrose, D-mannitol, starch, crystalline cellulose, light silicic acid anhydride, etc. Examples of the lubricant include magnesium stearate, calcium stearate, talc, colloidal silica, etc. Examples of the binder include crystalline cellulose, sucrose, D-mannitol, dextrin, hydroxypropyl cellulose, hydroxypropylmethyl cellulose, polyvinylpyrrolidone, etc. Examples of the disintegrating agent include starch, carboxymethyl cellulose, carboxymethyl cellulose calcium, croscarmellose sodium, sodium carboxymethyl starch, etc. Examples of the base for suppository include macrogol, etc. Examples of the solvent include water for injection, alcohol, propyleneglycol, macrogol, sesame oil, corn oil, etc. Examples of the solubilizer include polyethyleneglycol, propyleneglycol, D-mannitol, benzyl benzoate, ethanol, trisaminomethane, cholesterol, triethanolamine, sodium carbonate, sodium citrate, etc. Examples of the suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; etc. Examples of the isotonizing agent include sodium chloride, glycerin, D-mannitol, etc. Examples of the buffer include a buffer solution of phosphate, acetate, carbonate, citrate, etc. Examples of the soothing agent include benzylalcohol, etc. Examples of the preservative include paraoxybenzoic acid esters, chlorobutanol, benzylalcohol, phenethylalcohol, dehydroacetic acid, sorbic acid, etc. Examples of the antioxidant include sulfites, ascorbic acid, etc.

The compound of the present invention or a salt thereof may be used in combination with other drugs for the treatment or prevention of infectious disease of HIV (in particular, a pharmaceutical composition for the treatment or prevention of AIDS). In this case, these drugs can be formulated by mixing individually or simultaneously with pharmaceutically acceptable carriers, excipients, binders, diluents or the like, which can be administered orally or non-orally as a pharmaceutical composition for the treatment or prevention of infectious disease of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and the same subject (e.g. a kit for tablets to be administered simultaneously or with time intervals, characterized by having two or more tablets each comprising an agent and said tablets being put in one or separate bags and, if necessary, a column to describe time of administration of each agent, etc.), etc. are also included by the pharmaceutical composition of the present invention.

Examples of the other drug for the treatment or prevention of infectious diseases of HIV to be employed in combination with the compound of the present invention or a salt thereof include a compound which is difficult to be employed as a starting material for the preparation of the multiple-agents-binding compound of the present invention, such as a compound having anti-HIV activity but having no functional group (e.g., hydroxy group, carboxyl group, amino group, etc.) which is necessary for the preparation of the multiple-agents-binding compound of the present invention, etc. Specific examples of said other drug include HIV reverse transcriptase inhibitor which is a nucleoside derivative such as adefovir (9-(2-(phosphonylmethoxy)ethyl)adenine), adefovir dipivoxil, fozivudine tidoxil, 9-(2-(phosphonylmethoxy)propyl)adenine (PMPA), 9-(2-methylene-3-(phosphonylmethoxy)propyl)guanine, etc.; HIV reverse transcriptase inhibitor which is a non-nucleoside derivative such as nevirapine, efavirenz, etc.; etc.

The multiple-agents-binding compound of the present invention, the double-agents-binding compound of the present invention or a salt thereof can be produced by per se known method, for example, the following method:

When the compound of the present invention is produced by binding the compound having anti-HIV activity or a salt thereof through carboxyl group in its molecule with the other compound having anti-HIV activity or a salt thereof, amide linkage or ester linkage can be formed between said carboxyl group and amino group or hydroxy group of the above-mentioned compound having anti-HIV activity. In this case, when said compound having anti-HIV activity has another functional group which does not relate to the reaction forming the linkage, said another functional group may be protected. Said linkage may be formed by direct binding of the carboxyl group and the amino or hydroxy group, or through an appropriate spacer to obtain a linkage which is capable of being cleaved in vivo.

When the compound of the present invention is produced by binding the compound having anti-HIV activity or a salt thereof through hydroxy group in its molecule with the other compound having anti-HIV activity or a salt thereof, ester linkage can be formed between said hydroxy group and carboxyl group of the above-mentioned compound having anti-HIV activity. In this case, when said compound having anti-HIV activity has another functional group which does not relate to the reaction forming the linkage, said another functional group may be protected. Said linkage may be formed by direct binding of the hydroxy group and the carboxyl group, or through an appropriate spacer to obtain a linkage which is capable of being cleaved in vivo.

When the compound of the present invention is produced by binding the compound having anti-HIV activity or a salt thereof through said hydroxy group in its molecule with a functional group (e.g. amino group) of the other compound having anti-HIV activity or a salt thereof, said hydroxy group in the compound having anti-HIV activity and said amino group in the other compound having anti-HIV activity can be bound through a multiple-functional spacer having functional groups which can chemically bind to both of the hydroxy group in the compound having anti-HIV activity and the amino group in the other compound having anti-HIV activity.

Examples of the multiple-functional spacer include a spacer having a carboxyl group which can bind to the hydroxy group in the compound having anti-HIV activity and another carboxyl group which can bind to the amino group in the other compound having anti-HIV activity and more specifically a cyclic or acyclic compound having two or more carboxyl groups, etc. Among others, an aliphatic compound is preferable. In addition, said multiple-functional spacer may have the other functional group, as far as said functional group does not prevent the compound having anti-HIV activity from binding to the multiple-functional spacer.

Preferred examples of the aliphatic compound having two or more carboxyl groups as the multiple-functional spacer include $C_{3-12}$ aliphatic dicarboxylic acid, in view of simplicity and convenience of synthesis, ability to be cleaved with enzyme in vivo, anti-HIV activity of the compound of the present invention, etc., and $C_{3-8}$ aliphatic dicarboxylic acid is more preferable.

Among the dicarboxylic acid, succinic acid, glutaric acid or a derivative thereof is particularly preferable. Further, the multiple-functional spacer may be the above-mentioned aliphatic dicarboxylic acid (e.g. succinic acid, glutaric acid, etc.) bound to an amino acid (e.g. glycine, alanine, etc.).

Examples of the salt of the compound having anti-HIV activity to be employed as starting materials in the above-mentioned production include the same ones as the compound of the present invention.

In the above-mentioned production, when the compound having anti-HIV activity to be employed as starting materials has functional group such as amino group, carboxyl group, hydroxy group, etc. which is not involved in the reaction, these groups may be protected with a protective group which is usually employed in the field of peptide chemistry. If necessary, said protective group can be removed after the reaction to obtain the desired compound.

Examples of the protective groups for amino group include, for example, an optionally substituted $C_{1-6}$ alkyl carbonyl (for example, acetyl, propionyl, etc.), formyl, benzoyl, $C_{1-6}$ alkyloxycarbonyl (for example, methoxycarbonyl, ethoxycarbonyl, t-butoxycarbonyl, etc.), phenyloxycarbonyl, $C_{7-10}$ aralkyloxy-carbonyl (for example, benzyloxycarbonyl, etc.), trityl, phthaloyl, etc., each of which maybe substituted with 1–3 substituents selected from the class consisting of halogen atom (for example, fluorine, chlorine, bromine, iodine, etc.), $C_{1-6}$ alkyl carbonyl (for example, acetyl, propionyl, butyryl, etc.), nitro, etc.

Examples of the protective groups for the carboxyl group include, for example, an optionally substituted $C_{1-6}$ alkyl (for example, methyl, ethyl, propyl, isopropyl, butyl, t-butyl, etc.), phenyl, trityl, silyl, etc., each of which may be substituted with 1–3 substituents selected from the class consisting of halogen atom (for example, fluorine, chlorine, bromine, iodine, etc.), $C_{1-6}$alkylcarbonyl (for example, acetyl, propionyl, butyryl, etc.), formyl, nitro, etc.

Examples of the protective groups for the hydroxy group include, for example, an optionally substituted $C_{1-6}$ alkyl (for example, methyl, ethyl, propyl, isopropyl, butyl, t-butyl, etc.), phenyl, $C_{7-10}$ aralkyl (for example, benzyl, etc.), $C_{1-6}$ alkyl-carbonyl (for example, acetyl, propionyl, etc.), formyl, phenyloxycarbonyl, $C_{7-10}$, aralkyloxycarbonyl (for example, benzyloxycarbonyl, etc.), pyranyl, furyl, silyl, etc., each of which may be substituted with 1–4 substituents selected from the class consisting of halogen atom (for example, fluorine, chlorine, bromine, iodine, etc.), $C_{1-6}$ alkyl (for example, methyl, ethyl, propyl, isopropyl, butyl, t-butyl, etc.), phenyl, $C_{7-10}$ aralkyl (for example, benzyl, etc.), nitro group, etc.

These protective group may be introduced or removed by per se known methods (e.g. a method described in Protective Groups in Organic Chemistry (J. F. W. McOmie et al.; Plenum Press Inc.) or the methods analogous thereto. For example, employable methods for removing the protective groups are methods using an acid, a base, reduction, ultraviolet ray, hydrazine, phenylhydrazine, sodium N-methyldithiocarbamate, tetrabutylammonium fluoride, palladium acetate, etc.

When the compound of the present invention is produced by forming amide linkage between the carboxyl group of the compound having anti-HIV activity and the amino group of the other compound having anti-HIV activity, condensation reaction is carried out according to usual methods of peptide synthesis. Said methods for peptide synthesis are employed according to optional known methods, for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K.K.,1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphonate (DEPC), etc.

The condensation reaction can be carried out in a solvent. Examples of the solvents to be employed in the reaction include anhydrous or hydrous N,N-dimethylformamide (DMF), dimethylsulfoxide, pyridine, chloroform, dichloromethane, tetrahydrofuran, dioxane, acetonitrile, or a suitable mixture of these solvents. The reaction temperature is generally about −20° C. to about 50° C., preferably about −10° C. to about 30° C. and the reaction time is generally about 1 to about 100 hours, preferably about 2 to about 40 hours.

The thus obtained compound of the present invention can be isolated and purified by known separation and purification methods such as concentration, concentration under reduced pressure, extraction, crystallization, recrystallization, solvent conversion, chromatography, etc.

When the compound of the present invention is produced by forming ester linkage between the carboxyl group of the compound having anti-HIV activity and the hydroxy group of the other compound having anti-HIV activity, per se known methods, for example, the same production methods, reaction conditions and separation and purification methods as employed in the above-mentioned amide linkage formation reaction can be employed.

When the compound of the present invention is produced by forming a linkage through a multiple-functional spacer, for example, aliphatic dicarboxylic acid (e.g. succinic acid, glutaric acid) between the hydroxy group of the compound having anti-HIV activity and the other functional group, for example, amino group of the other compound having anti-HIV activity, a compound wherein the hydroxy group of the compound having anti-HIV activity is bound to the multiple-functional spacer is first produced. That is, for example, in the presence of dimethylaminopyridine, the compound having anti-HIV activity (e.g., HIV reverse transcriptase inhibitor which is a nucleoside derivative, etc.) having hydroxy group is reacted with succinic anhydride or glutaric anhydride to obtain a compound wherein the compound having anti-HIV activity is bound to succinic acid or glutaric acid as multiple-functional spacer through ester linkage. Then, the obtained compound is condensed with the other compound having anti-HIV activity having, for example, amino group according to the above-mentioned methods for peptide synthesis.

The thus obtained compound of the present invention can be isolated and purified by known separation and purification methods such as concentration, concentration under reduced pressure, extraction, crystallization, recrystallization, solvent convert, chromatography, etc.

The multiple-agents-binding compound of the present invention, the double-agents-binding compound of the present invention or a salt thereof can be used for the treatment or prevention of various infectious diseases of HIV, for example, AIDS in human and also for the prevention of the progression of AIDS. Said compound is also low in toxicity and safely used.

The dose per day of multiple-agents-binding compound of the present invention, the double-agents-binding compound of the present invention or a salt thereof varies depending on the condition and body weight of a patient, administration route, etc. Typical daily dose per adult patient (body weight: 50 Kg) for oral administration is about 5–2000 mg, preferably about 10–1000 mg, and more preferably about 20–700 mg as active ingredient and said compound is administered once or 2–3 times per day.

When the multiple-agents-binding compound of the present invention, the double-agents-binding compound of the present invention or a salt thereof is used in combination with other drug for the treatment or prevention of infectious diseases of HIV, the dose of the other drug ranges, for example, from about 1/200–1/2 or more of usual dose to about 2–3 times or less of usual dose.

EFFECT OF THE INVENTION

The multiple-agents-binding compound of the present invention, the double-agents-binding compound of the present invention or a salt thereof is expected to be more effective than conventional cocktail therapy and is advantageously used for the prevention and treatment of various infectious diseases of HIV in human, for example, AIDS, and for the prevention of the progression of AIDS.

In addition, the compound of the present invention has more potent anti-HIV activity, is improved in absorption when orally administered, stability, physicochemical properties, etc., solves the problems in complexity of administration time or dose, etc., ease of treatment, and reduces toxicity according to reduction of dose and shortened period for administration. Therefore, the compound of the present invention can be used as simple, convenient and effective agent which can be substituted for conventional cocktail therapy.

EXAMPLES

The present invention is hereinafter described in more detail by means of the following Test Example, Formulation Example, Reference Example and Working Example, which are mere examples of the present invention and are not construed as limitative to the present invention.

In the present specification, each symbol shown below has the following meaning:
tBu: t-butyl
Boc: t-butoxycarbonyl
Thz: (R)-1,3-thiazolidine-4-carbonyl
DMAP: 4-(dimethylamino)pyridine
DCC: N,N'-dicyclohexylcarbodiimide
DMF: N,N'-dimethylformamide
HOBt: 1-hydroxybenzotriazole
EDC: N-ethyl-N'-[3-(dimethylamino)propyl]carbodiimide
Apns: (2S,3S)-3-amino-2-hydroxy-4-phenylbutanoyl
Dmt: (R)-5,5-dimethyl-1,3-thiazolidine-4-carbonyl
AZT: 3'-azido-3'-deoxythymidine

Test Examples

(1) HIV Protease Inhibitory Activity

HIV protease inhibitory activity of the compounds of the present invention [Compounds of Working Examples 1–7] was evaluated according to the test method already reported in the literature (Journal of Synthetic Organic Chemistry, Japan, 52,403–412 (1994), Japanese Patent Unexamined Publication No. 1993-170722, etc.). In addition, using Compounds of Reference Examples 1–4, similar test was carried out.

Instead of natural HIV protease, recombinant HIV protease already reported in the literature (cf. Science, 230, 949 (1985)) was used for the evaluation of HIV protease inhibitory activity (cf. Japanese Patent Unexamined Publication No. 1993-170722, etc.). As the substrate of said recombinant HIV protease, synthetic nonapeptide substrate (Ac-Arg-Ala-Ser-Gln-Asn-Tyr-Pro-Val-Val-$NH_2$ trifluoroacetate) was used, and protease activity was determined.

Fifteen µl of the reaction solution containing 100 mM (final concentration) of MES buffer solution (pH5.5), 40 mM of said substrate, 9.2 µg of said recombinant HIV protease, and various concentration of Test Compound (for example, Test Compound was previously dissolved in DMSO, etc.) was used, and the reaction was started after said recombinant HIV protease had been added to the reaction solution. The reaction was carried out at 37° C. for 60 minutes, and then, the reaction was stopped by addition of 15 µl of acetonitrile. The amount of the peptide fragment produced by cleaving the substrate between -Tyr . . . Pro- of said substrate was determined according to the internal standard method of reverse phase HPLC. When the concentration of test compound was zero, protease activity was defined as 100%; when the peptide fragment was not detected, remaining protease activity was defined as 0%; and remaining protease activity was calculated based on the determined concentration of the peptide fragment. When the remaining protease activity was 0%, inhibition rate which indicates activity inhibiting HIV protease was defined as 100%, and the inhibition rate was defined according to the value taken the remaining protease activity indicated by said percentage from 100%.

(2) Anti-HIV Activity

Anti-HIV activity of the compounds of the present invention was evaluated according to the method described below.

The inhibitory effect on virus particle formation of HIV virus with which T cell lymphocytes were infected was evaluated according to ability to prevent T cell lymphocytes infected with said HIV virus from dying.

According to the test method described in the literature (O. S. Weislow et al., J. Natl. Cancer Inst., 81, 577 (1989), etc.), anti-HIV activity of the compounds of the present invention was evaluated. As the T cell lymphocytes, CEMM-SS cells were used. As the HIV virus, HIV-1 IIIB (HTLV-IIIB) virus which is HIV type 1 virus was used. On 96 well microtiter plate containing 200 µl of culture medium (RPMI-1640 medium containing 50 µg/ml of gentamicin and 10% fetal calf serum), determined concentration of Test Compound and HIV-1 IIIB virus (the mount of virus per well is that necessary for completely killing infected cells 6 days after infection), CEMM-SS cell ($2.5 \times 10^4$ cells/ml) were inoculated and cultivated at 37° C. for 6 days in the incubator containing 5% $CO_2$. Thereafter, the number of living cells was determined by the MTT method (R. Pauwels et al., J. Virol. Methods, 20, 309 (1988), etc.), and the determined value was defined as (ODT)HIV. HIV-non-infected CEMM-SS cells and HIV-infected CEMM-SS cells were respectively cultivated under the same conditions provided that the concentration of Test Compound was zero. Thereafter, the number of living cells was determined, and the respectively determined value was defined as $(OD_C)_{MOCK}$ and $(OD_C)_{HIV}$. Using these values, $(OD_T)_{HIV}$, $(OD_C)_{MOCK}$ and $(OD_C)_{HIV}$, inhibitory rate, ratio preventing T cell lymphocytes infected with said HIV virus from dying, was calculated according to the following formula:

$$[(OD_T)_{HIV} - (OD_C)_{HIV}]/[(OD_C)_{MOCK} - (OD_C)_{HIV}]$$

Based on $EC_{50}$ which is the concentration of Test Compound making the calculated inhibitory rate 50%, anti-HIV activity was evaluated.

The results of HIV protease inhibitory activity and anti-HIV activity of the compound of the present invention evaluated by the above-mentioned methods were shown in Table 1, together with the results of Compound of Reference Example. In Table 1, HIV protease inhibitory activity is shown as the inhibitory rate when the final concentration of Test Compound in the reaction solution was 5 µM, and the values in parentheses correspond to the inhibitory rate when the final concentration of Test Compound in the reaction solution was 50 nM.

TABLE 1

| Test Compound | Inhibition of Anti-HIV activity ($EC_{50}$) | |
|---|---|---|
| | HIV protease | HIV-1 IIIB/ CEMM-SS |
| Compound of Ref. Ex. 1 | 93% (20%) | |
| Compound of Ref. Ex. 2 | 99% (76%) | |
| Compound of Ref. Ex. 3 | 87% | |
| Compound of Ref. Ex. 4 | 100% (78%) | |
| Compound of Working Ex. 4 | 11% | 3.8 nM |
| Compound of Working Ex. 5 | 57% | 8.9 nM |
| Compound of Working Ex. 6 | 83% | 0.24 nM |
| Compound of Working Ex. 7 | 96% (39%) | 7.3 nM |
| AZT | | 11 nM |

Formulation Examples

The pharmaceutical composition (e.g. a medicament for the treatment or prevention of infectious disease of HIV, a medicament for the treatment or prevention of AIDS, etc.) comprising the compound of the present invention or a salt thereof of the present invention, as an active ingredient, can be prepared, for example, by the following prescriptions:

| 1. Capsule | |
|---|---|
| (1) Compound obtained in Working Example 6 | 70 mg |
| (2) lactose | 120 mg |
| (3) fine crystalline cellulose | 9 mg |
| (4) magnesium stearate | 1 mg |
| 1 capsule | 200 mg |

(1), (2), (3) and ½ of (4) are mixed and then granulated. To the granules is added the remainder of (4), and the whole is filled into a gelatin capsule.

| 2. Tablet | |
|---|---|
| (1) Compound obtained in Working Example 6 | 70 mg |
| (2) lactose | 94 mg |
| (3) corn starch | 30 mg |
| (4) fine crystalline cellulose | 5 mg |
| (5) magnesium stearate | 1 mg |
| 1 tablet | 200 mg |

(1), (2), (3), ⅔ of (4) and ½ of (5) are mixed and then granulated. To the granules are added the remainders of (4) and (5), followed by subjecting the mixture to compression molding.

Reference Example 1

(R)-N-t-butyl-3-[(2S,3S)-3-(3,3-dimethylsuccinyl)amino-2-hydroxy-4-phenylbutyryl]-1,3-thiazolidine-4-carboxamide (KNI-391)

The title compound was prepared according to the method described in Japanese Patent Unexamined Publication No. 259532-1996.

In a mixture of chloroform-DMF (1:1) was dissolved 2,2-dimethyl succinic acid (176 mg), and to the solution was added DCC (248 mg). The mixture was stirred at room temperature for 3 hours, and insoluble materials were filtered off. To the filtrate was added under ice-cooling (R)-3-[(2S,3S)-3-amino-2-hydroxy-4-phenylbutyryl]-1,3-thiazolidine-4-N'-t-butylcarboxamide [prepared by the method described in Science 248, 358 (1990); Bioorg. & Med. Chem. Lett., 4, 2273 (1994); etc.] (400 mg), and the mixture was stirred overnight at room temperature. The reaction solution was concentrated under reduced pressure, and the residue was dissolved in ethyl acetate. The solution was successively washed with 5% citric acid solution and saturated brine, and dried with anhydrous sodium sulfate. The solvent was evaporated under reduced pressure, and the residue was recrystallized from n-hexane to give the title compound (467 mg).

m.p. 99–102° C.

TOF-MS [M+H]$^+$ 494

Reference Example 2

(R)-N-t-butyl-3-[(2S,3S)-3-(3,3-dimethylsuccinyl)amino-2-hydroxy-4-phenylbutyryl]-5,5-dimethyl-1,3-thiazolidine-4-carboxamide (KNI-413)

According to substantially the same method as described in Reference Example 1, the title compound was prepared from 2,2-dimethyl succinic acid and (R)-3-[(2S,3S)-3-amino-2-hydroxy-4-phenylbutyryl]-5,5-dimethyl-1,3-thiazolidine-4-N'-t-butylcarboxamide (prepared by the method described in Japanese Patent Unexamined Publication No. 1996-259532).

m.p. 98–102° C.

TOF-MS [M+H]$^+$ 522

Reference Example 3

(R)-N-(2-methylbenzyl)-3-[(2S,3S)-3-(3,3-dimethylsuccinyl)amino-2-hydroxy-4-phenylbutyryl]-1,3-thiazolidine-4-carboxamide (KNI-689)

According to substantially the same method as described in Reference Example 1, the title compound was prepared from 2,2-dimethyl succinic acid and (R)-3-[(2S,3S)-3-amino-2-hydroxy-4-phenylbutyryl]-1,3-thiazolidine-4-N'-(2-methylbenzyl)carboxamide (prepared by the method described in Japanese Patent Unexamined Publication No. 1998-101654). m.p. 103–104° C.

TOF-MS [M+H]$^+$ 542

Reference Example 4

(R)-N-(2-methylbenzyl)-3-[(2S,3S)-3-(3,3-dimethylsuccinyl)amino-2-hydroxy-4-phenylbutyryl]-5,5-dimethyl-1,3-thiazolidine-4-carboxamide (KNI-852)

According to substantially the same method as described in Reference Example 1, the title compound was prepared from 2,2-dimethyl succinic acid and (R)-3-[(2S,3S)-3-amino-2-hydroxy-4-phenylbutyryl]-5,5-dimethyl-1,3-thiazolidine-4-N'-(2-methylbenzyl)carboxamide (prepared by the method described in Japanese Patent Unexamined Publication No. 1998-25242).

m.p. 100–102° C.

TOF-MS [M+H]$^+$ 570

Working Example 1

{(2S,5R)-3-azido-5-[5-methyl-2,4-dioxo-3,4-dihydro-1(2H)-pyrimidinyl]tetrahydro-2-furanyl}methyl 4-[((1S,2S)-1-benzyl-3-{(4R)-4-[(t-butylamino)carbonyl]-1,3-thiazolidin-3-yl}-2-hydroxy-3-oxopropyl)amino]-2,2-dimethyl-4-oxobutanoate To a solution of (R)-N-t-butyl-3-[(2S,3S)-3-(3,3-dimethylsuccinyl)amino-2-hydroxy-4-phenylbutyryl]-1,3- thiazolidine-4-carboxamide (Compound of Reference Example 1: 240 mg) in dichloromethane were added under ice-cooling AZT (52 mg), DMAP (5 mg) and DCC (100 mg), and the mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (147 mg).

m.p. 83–84° C.

FAB-MS m/z 743.3176([M+H]$^+$)

Working Example 2

{(2S,5R)-3-azido-5-[5-methyl-2,4-dioxo-3,4-dihydro-1(2H)-pyrimidinyl]tetrahydro-2-furanyl}methyl 4-[((1S,2S)-1-benzyl-3-{(4R)-4-[(t-butylamino)carbonyl]-1,3-thiazolidin-3-yl}-2-hydroxy-3-oxopropyl)amino]-2,3-dimethyl-4-oxobutanoate In a mixture of chloroform-DMF (1:1) was dissolved 2,3-dimethyl succinic acid (30 mg), and to the solution was added DCC (43 mg). The mixture was stirred at room temperature for 3 hours, and insoluble materials were filtered off. To the filtrate were added under ice-cooling AZT (56 mg) and DMAP (2 mg), and the mixture was stirred overnight at room temperature. The reaction solution was concentrated under reduced pressure, and to a solution of the residue in DMF were added under ice-cooling (R)-3-[(2S,3S)-3-amino-2-hydroxy-4-phenylbutyryl]-1,3 -thiazolidine-4-N'-t-butylcarboxamide (70 mg), HOBt.H$_2$O (32 mg) and DCC (43 mg). The mixture was stirred overnight at room temperature, and insoluble materials were filtered off. The filtrate was concentrated under reduced pressure, and the residue was dissolved in ethyl acetate. The solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (115 mg).

m.p. 102–103° C.

FAB-MS m/z 743.3202([M+H]$^+$)

Working Example 3

{(2S,5R)-3-azido-5-[5-methyl-2,4-dioxo-3,4-dihydro-1(2H)-pyrimidinyl]tetrahydro-2-furanyl}methyl 4-[((1S,2S)-1-benzyl-3-{(4R)-5,5-dimethyl-4-[(t-butylamino)carbonyl]-1,3-thiazolidin-3-yl}-2-hydroxy-3-oxopropyl)amino]-2,2-dimethyl-4-oxobutanoate To a solution of (R)-N-t-butyl-3-[(2S,3S)-3-(3,3-dimethylsuccinyl)amino-2-hydroxy-4-phenylbutyryl]-5,5-dimethyl-1,3-thiazolidine-4-carboxamide (Compound of Reference Example 2: 244 mg) in dichloromethane were added under ice-cooling AZT (50 mg), DMAP (4 mg) and DCC (95 mg), and the mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (138 mg).

m.p. 95–97° C.

FAB-MS m/z 771.3508([M+H]$^+$)

Working Example 4

{(2S,5R)-3-azido-5-[5-methyl-2,4-dioxo-3,4-dihydro-1(2H)-pyrimidinyl]tetrahydro-2-furanyl}methyl 4-{[(1S,2S)-1-benzyl-2-hydroxy-3-((4R)-4-{[(2-methylbenzyl)aminolcarbonyl}-1,3-thiazolidin-3-yl)-3-oxopropyl]amino)-2,2-dimethyl-4-oxobutanoate To a solution of (R)-N-(2-methylbenzyl)-3-[(2S,3S)-3-(3,3-dimethylsuccinyl)amino-2-hydroxy-4-phenylbutyryl]-1,3-thiazolidine-4-carboxamide (Compound of Reference Example 3: 197 mg) in dichloromethane were added under ice-cooling AZT (50 mg), DMAP (4 mg) and DCC (67 mg), and the mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (136 mg).

m.p. 102–103° C.

FAB-MS m/z 791.3205([M+H]$^+$)

Working Example 5

{(2S,5R)-3-azido-5-[5-methyl-2,4-dioxo-3,4-dihydro-1(2H)-pyrimidinyl]tetrahydro-2-furanyl}methyl 4-([(1S,2S)-1-benzyl-2-hydroxy-3-((4R)-4-([(2-methylbenzyl)amino]carbonyl}-1,3-thiazolidin-3-yl)-3-oxopropyl]amino)-2,3-dimethyl-4-oxobutanoate In a mixture of chloroform-DMF (1:1) was dissolved 2,3-dimethyl succinic acid (34 mg), and to the solution was added DCC (48 mg). The mixture was stirred at room temperature for 3 hours. Insoluble materials were filtered off, and to the filtrate were added under ice-cooling AZT (57 mg) and DMAP (2 mg). The mixture was stirred overnight at room temperature, and the reaction solution was concentrated under reduced pressure. To a solution of the residue in DMF were added under ice-cooling (R)-3-[(2S,3S)-3-amino-2-hydroxy-4-phenylbutyryl]-1,3-thiazolidine-4-N'-(2-methylbenzyl)carboxamide (80 mg), HOBt.H$_2$O (33 mg) and DCC (44 mg), and the mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (120 mg).

m.p. 114–115° C.

FAB-MS m/z 791.3230([M+H]$^+$)

Working Example 6

{(2S,5R)-3-azido-5-[5-methyl-2,4-dioxo-3,4-dihydro-1(2H)-pyrimidinyl]tetrahydro-2-furanyl}methyl 4-{(1S,2S)-1-benzyl-3-((4R)-5,5-dimethyl-4-{[(2-methylbenzyl)amino]carbonyl)-1,3-thiazolidin-3-yl)-2-hydroxy-3-oxopropyl]amino}-2,2-dimethyl-4-oxobutanoate To a solution of (R)-N-(2-methylbenzyl)-3-[(2S,3S)-3-(3,3-dimethylsuccinyl)amino-2-hydroxy-4-phenylbutyryl]-5, 5-dimethyl-1,3-thiazolidine-4-carboxamide (Compound of Reference Example 4: 266 mg) in dichloromethane were added under ice-cooling, AZT (50 mg), DMAP (3 mg) and DCC (87 mg), and the mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (163 mg).

m.p. 107–108° C.

FAB-MS m/z 819.3533([M+H]$^+$)

Working Example 7

{(2S,5R)-3-azido-5-[5-methyl-2,4-dioxo-3,4-dihydro-1(2H)-pyrimidinyl]tetrahydro-2-furanyl}methyl 4-([(1S,2S)-1 -benzyl-3-((4R)-5,5-dimethyl-4-{[(2-methylbenzyl)amino]carbonyl}-1,3-thiazolidin-3-yl)-2-hydroxy-3-oxopropyl]amino}-2, 3-dimethyl-4-oxobutanoate In a mixture of chloroform-DMF (1:1) was dissolved 2,3-dimethyl succinic acid (29 mg), and to the solution was added DCC (41 mg). The mixture was stirred at room temperature for 3 hours, and insoluble materials were filtered off. To the filtrate were added under ice-cooling AZT (53 mg) and DMAP (2 mg), and the mixture was stirred overnight at room temperature. The reaction solution was concentrated under reduced pressure, and to a solution of the residue in DMF were added under ice-cooling (R)-3-[(2S, 3S)-3-amino-2-hydroxy-4-phenylbutyryl]-5,5-dimethyl-1, 3-thiazolidine-4-N'-(2-methylbenzyl)carboxamide (80 mg), HOBt.H$_2$O (31 mg) and DCC (41 mg). The mixture was stirred overnight at room temperature. Insoluble materials were filtered off, and the filtrate was concentrated under reduced pressure. The residue was dissolved in ethyl acetate, and the solution was successively washed with 5% citric acid solution, 5% sodium hydrogencarbonate solution and saturated brine, and dried with anhydrous sodium sulfate. The solvent was evaporated under reduced pressure, and the residue was recrystallized from n-hexane to give the title compound (133 mg).

m.p. 116–118° C.

FAB-MS m/z 819.3546([M+H]$^+$)

Reference Example 5

H-Gly-AZT hydrochloride

In a mixture of chloroform-DMF (1:1) was dissolved AZT (1.0 g), and to the solution were added under ice-cooling Boc-Gly-OH (1.32 g) and DMAP (0.46 g). The mixture was stirred overnight. The reaction solution was concentrated under reduced pressure, and the residue was dissolved in ethyl acetate. The solution was successively washed with 5% citric acid solution, 5% sodium hydrogencarbonate solution and saturated brine, dried with anhydrous sodium sulfate, and concentrated under reduced pressure. To the residue was added n-hexane, and precipitates were filtered to give white powder. To the white powder were added anisole (0.25 ml) and 4N HCl/dioxane (5 ml), and the mixture was stirred at room temperature for 1 hour. The reaction solution was concentrated under reduced pressure, and to the residue was added diethylether. Precipitates were filtered to give the title compound as white powder.

Working Example 8

2,6-dimethylphenoxyacetyl-Apns(succinyl-Gly-AZT)-Dmt-NH-tBu

In a mixture of chloroform-DMF (1:1) was dissolved 2,6-dimethylphenoxyacetyl-Apns-Dmt-NH-tBu (KNI-727) (150 mg), which was synthesized according to a method described in J. Med. Chem., 42, 1789 (1999), and to the solution were added under ice-cooling succinic anhydride (54 mg) and DMAP (6.6 mg). The mixture was stirred overnight. The reaction solution was concentrated under reduced pressure, and the residue was dissolved in ethyl acetate. The solution was washed with saturated brine, dried with anhydrous sodium sulfate, and concentrated under reduced pressure. The residue was dissolved in DMF, and to the solution were added under ice-cooling H-Gly-AZT hydrochloride (293 mg) obtained in Reference Example 5, HOBt.H$_2$O (111 mg) and EDC HCl (139 mg). The mixture was stirred overnight. The reaction solution was concentrated under reduced pressure, and the residue was dissolved in ethyl acetate. The solution was successively washed with 5% citric acid solution and saturated brine, dried with anhydrous sodium sulfate, concentrated under reduced pressure, and the residue was subjected to freeze-drying to give crude product of the title compound, which was purified with HPLC to give purified product of the title compound.

Yield: 34.3 mg m.p. 112.8–117.0° C.

[α]–4.69° (C=0.06, MeOH)

HRFAB-MS m/z 962.4090([M+H]$^+$)

Working Example 9

2,6-dimethylphenoxyacetyl-Apns(glutaryl-Gly-AZT)-Dmt-NH-tBu

In a mixture of chloroform-DMF (1:1) was dissolved 2,6-dimethylphenoxyacetyl-Apns-Thz-NH-tBu (200 mg), which was synthesized according to a method described in J. Med. Chem., 42, 1789 (1999), and to the solution were added under ice-cooling glutaric anhydride (62 mg) and DMAP (22 mg). The mixture was stirred overnight. The reaction solution was concentrated under reduced pressure, and the residue was dissolved in ethyl acetate. The solution was washed with saturated brine, dried with anhydrous sodium sulfate, and concentrated under reduced pressure. The residue was dissolved in DMF, and to the solution were added under ice-cooling HOBt.H$_2$O (172 mg) and EDC.HCl (214 mg). The mixture was stirred at room temperature for 20 minutes, and to the mixture was added H-Gly-AZT hydrochloride (227 mg) obtained in Reference Example 5. The mixture was stirred overnight. The reaction solution was concentrated under reduced pressure, and the residue was dissolved in ethyl acetate. The solution was successively washed with 5% citric acid solution and saturated brine, dried with anhydrous sodium sulfate, concentrated under reduced pressure, and the residue was subjected to freeze-drying to give crude product of the title compound, which was purified with HPLC to give purified product of the title compound.

Yield: 55.5 mg m.p. 93.5–95.5° C.

[α]–4.769° (c=0.06, meoh)

HRFAB-MS m/z 976.4229([m+h]$^+$)

What is claimed is:

1. A compound comprising:
   at least two compounds having anti-HIV activity and having no affinity for cell surface proteins;
   said compounds bound together with at least one linkage selected from the group consisting of an —OC(O)— linkage, an amide linkage, an ether linkage and a disulfide linkage.

2. The compound of claim 1 wherein said compounds are selected from the group consisting of an HIV reverse transcriptase inhibitor, an HIV protease inhibitor and a CCR5 antagonist.

3. The compound according to claim 1, wherein at least one of said compounds is a CCR5 antagonist.

4. A compound comprising:
   an HIV reverse transcriptase inhibitor and an HIV protease inhibitor;
   said HIV reverse transcriptase inhibitor and said HIV protease inhibitor bound together with at least one linkage selected from the group consisting of an —OC(O)— linkage, an amide linkage, an ether linkage and a disulfide linkage.

5. The compound according to claim 4, wherein said HIV reverse transcriptase inhibitor is a nucleoside derivative having at least one hydroxy group.

6. The compound according to claim 5, wherein said HIV reverse transcriptase inhibitor is zidovudine, didanosine, zalcitabine, lamivudine, stavudine or abacavir.

7. The compound according to claim 5, wherein said HIV reverse transcriptase inhibitor is zidovudine.

8. The compound according to claim 4, wherein said HIV protease inhibitor is a compound having at least one hydroxy group, amino group, carboxyl group or a combination thereof.

9. The compound according to claim 8, wherein said HIV protease inhibitor is saquinavir, ritonavir, indinavir, nelfinavir, a compound of the formula:

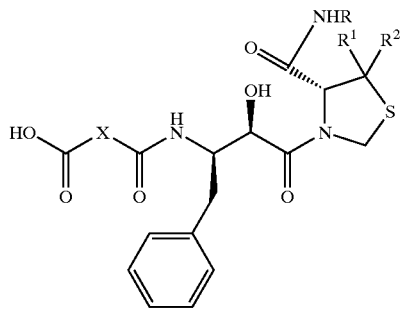

wherein R is a $C_{1-6}$ alkyl group or an unsubstituted or substituted phenyl-$C_{1-3}$ alkyl group, $R^1$ and $R^2$ are independently a hydrogen atom or a $C_{1-6}$ alkyl group, and X is an unsubstituted or substituted $C_{1-6}$ alkylene group, a compound of the formula:

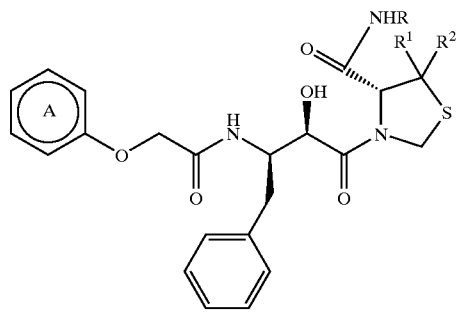

wherein R is a $C_{1-6}$ alkyl group or an unsubstituted or substituted phenyl-$C_{1-3}$ alkyl group, $R^1$ and $R^2$ are independently a hydrogen atom or a $C_{1-6}$ alkyl group, and the ring A is an unsubstituted or substituted benzene ring, or a salt thereof.

10. The compound according to claim 9, wherein said HIV protease inhibitor is a compound of the formula:

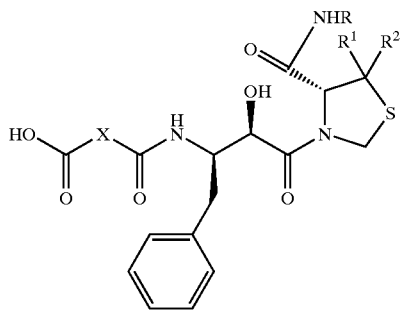

wherein R is a $C_{1-6}$ alkyl group or an unsubstituted or substituted phenyl-$C_{1-3}$ alkyl group, $R^1$ and $R^2$ are independently a hydrogen atom or a $C_{1-6}$ alkyl group, and X is an unsubstituted or substituted $C_{1-6}$ alkylene group, a compound of the formula:

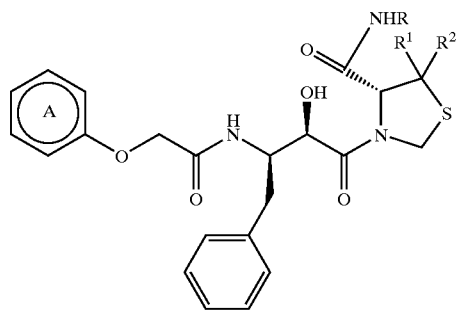

wherein R is a $C_{1-6}$ alkyl group or an unsubstituted or substituted phenyl-$C_{1-3}$ alkyl group, $R^1$ and $R^2$ are independently a hydrogen atom or a $C_{1-6}$ alkyl group, and the ring A is an unsubstituted or substituted benzene ring, or a salt thereof.

11. The compound according to claim 1, with at least two —OC(O)— linkages.

12. A compound selected from the group consisting of:
a compound of the formula:

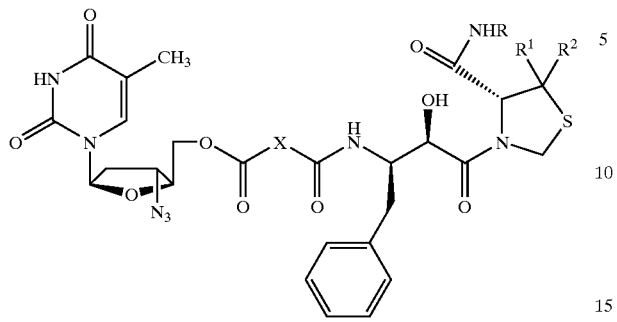

wherein R is a $C_{1-6}$ alkyl group or an unsubstituted or substituted phenyl-$C_{1-3}$ alkyl group,
$R^1$ and $R^2$ are independently a hydrogen atom or a $C_{1-6}$ alkyl group, and
X is an unsubstituted or substituted $C_{1-6}$ alkylene group;
a compound of the formula:

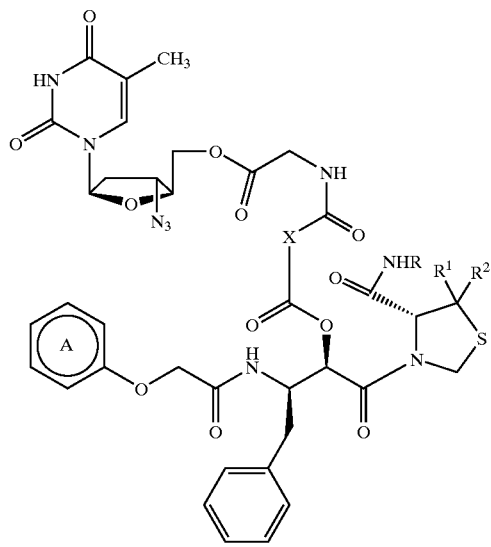

wherein R is a $C_{1-6}$ alkyl group or an unsubstituted or substituted phenyl-$C_{1-3}$ alkyl group,
$R^1$ and $R^2$ are independently a hydrogen atom or a $C_{1-6}$ alkyl group,
X is an unsubstituted or substituted $C_{1-6}$ alkylene group, and the ring A is an unsubstituted or substituted benzene ring,
and salts thereof.

13. The compound according to claim 12, wherein
R is a benzyl group substituted with a $C_{1-3}$ alkyl group or a t-butyl group,
$R^1$ and $R^2$ are independently a hydrogen atom or a methyl group, and
X is a group of the formula: —$(CH_2)_m$—
wherein m is an integer of 1–3;
and wherein a methylene of X may be further substituted with a methyl group.

14. A pharmaceutical composition comprising:
a compound of claim 12 and
at least one pharmaceutically acceptable carrier, excipient, binder or diluent.

15. A method for the treatment of AIDS, which comprises administering to a mammal in need thereof an effective amount of a compound as claimed in claim 12, or a salt thereof.

16. A method for the treatment of infectious diseases of HIV, which comprises administering to a mammal in need thereof an effective amount of a compound as claimed in claim 12, or a salt thereof.

17. A compound comprising:
an HIV reverse transcriptase inhibitor and an HIV protease inhibitor;
said HIV reverse transcriptase inhibitor and said HIV protease inhibitor bound together through a spacer;
wherein said spacer is a cyclic or acyclic group having at least two linkages,
wherein each linkage is independently selected from the group consisting of an —OC(O)— linkage, an amide linkage, an ether linkage and a disulfide linkage.

18. The compound according to claim 17, wherein said HIV reverse transcriptase inhibitor is a nucleoside derivative having at least one hydroxy group.

19. The compound according to claim 18, wherein said HIV reverse transcriptase inhibitor is zidovudine, didanosine, zalcitabine, lamivudine, stavudine or abacavir.

20. The compound according to claim 18, wherein said HIV reverse transcriptase inhibitor is zidovudine.

21. The compound according to claim 17, wherein said HIV protease inhibitor is a compound having at least one hydroxy group, amino group, carboxyl group or a combination thereof.

22. A pharmaceutical composition comprising:
a compound of claim 17 and
at least one pharmaceutically acceptable carrier, excipient, binder or diluent.

23. A method for the treatment of AIDS, which comprises administering to a mammal in need thereof an effective amount of a compound as claimed in claim 17, or a salt thereof.

24. A method for the treatment of infectious diseases of HIV, which comprises administering to a mammal in need thereof an effective amount of a compound as claimed in claim 17, or a salt thereof.

* * * * *